United States Patent
Farmer

(10) Patent No.: US 7,780,913 B2
(45) Date of Patent: Aug. 24, 2010

(54) PAINT FOR DETECTION OF CORROSION AND WARNING OF CHEMICAL AND RADIOLOGICAL ATTACK

(75) Inventor: Joseph C. Farmer, Tracy, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1057 days.

(21) Appl. No.: 11/293,675

(22) Filed: Dec. 1, 2005

(65) Prior Publication Data

US 2007/0048867 A1    Mar. 1, 2007

Related U.S. Application Data

(60) Provisional application No. 60/711,488, filed on Aug. 26, 2005.

(51) Int. Cl.
- G01N 31/00 (2006.01)
- G01N 21/76 (2006.01)
- G01N 21/64 (2006.01)
- G01N 21/00 (2006.01)
- C12Q 1/68 (2006.01)

(52) U.S. Cl. ......... 422/50; 422/52; 422/82.08; 422/55; 422/57; 422/82.05; 436/6

(58) Field of Classification Search ........... 422/50, 422/52, 82.08, 55, 57, 82.05; 436/6
See application file for complete search history.

(56) References Cited

U.S. PATENT DOCUMENTS

| | | | | |
|---|---|---|---|---|
| 3,858,124 A | * | 12/1974 | Bass et al. | 359/238 |
| 3,960,759 A | * | 6/1976 | Mallis | 436/104 |
| 4,017,370 A | | 4/1977 | Wootten | |
| 4,864,139 A | * | 9/1989 | Phillips | 250/367 |
| 5,032,380 A | | 7/1991 | Novak et al. | |
| 5,350,033 A | * | 9/1994 | Kraft | 180/167 |
| 5,859,537 A | * | 1/1999 | Davis et al. | 324/693 |
| 5,935,862 A | * | 8/1999 | Novak | 436/104 |
| 6,011,266 A | * | 1/2000 | Bell | 250/390.01 |
| 6,134,289 A | * | 10/2000 | Peurrung et al. | 376/153 |
| 6,218,846 B1 | | 4/2001 | Ludwig et al. | |
| 6,276,214 B1 | | 8/2001 | Kimura et al. | |
| 6,403,329 B1 | | 6/2002 | Novak et al. | |
| 6,644,917 B2 | | 11/2003 | Zhao et al. | |

(Continued)

FOREIGN PATENT DOCUMENTS

EP    0863396    9/1998

(Continued)

OTHER PUBLICATIONS

Zhang et al. "Corrosion-Sensing Behavior of an Acrylic-Based Coating System" Corrosion, 1999, pp. 957-967, vol. 555, No. 10.

(Continued)

*Primary Examiner*—Lore Jarrett
(74) *Attorney, Agent, or Firm*—Eddie E. Scott; John H. Lee

(57) ABSTRACT

A system for warning of corrosion, chemical, or radiological substances. The system comprises painting a surface with a paint or coating that includes an indicator material and monitoring the surface for indications of the corrosion, chemical, or radiological substances.

6 Claims, 4 Drawing Sheets

U.S. PATENT DOCUMENTS

| | | | |
|---|---|---|---|
| 6,809,358 B2 * | 10/2004 | Hsieh et al. | 257/291 |
| 7,595,494 B2 * | 9/2009 | Koltick et al. | 250/394 |
| 2002/0110844 A1 * | 8/2002 | Christner et al. | 435/11 |
| 2003/0032192 A1 | 2/2003 | Haubold et al. | |
| 2003/0068824 A1 | 4/2003 | Frankel et al. | |
| 2004/0035498 A1 | 2/2004 | Kinlen | |
| 2004/0109853 A1 | 6/2004 | McDaniel | |
| 2004/0168790 A1 * | 9/2004 | Hosoe et al. | 165/11.1 |
| 2005/0044989 A1 | 3/2005 | Liao | |
| 2005/0089142 A1 | 4/2005 | Marek | |
| 2005/0164169 A1 | 7/2005 | Malak | |
| 2007/0023665 A1 * | 2/2007 | Gallagher et al. | 250/358.1 |
| 2007/0048866 A1 * | 3/2007 | Farmer et al. | 436/2 |
| 2007/0117042 A1 * | 5/2007 | Barr et al. | 430/270.1 |
| 2009/0012745 A1 * | 1/2009 | Longman et al. | 702/179 |

FOREIGN PATENT DOCUMENTS

| | | |
|---|---|---|
| WO | WO 00/06796 A | 2/2000 |
| WO | WO 02/28973 A | 4/2002 |

OTHER PUBLICATIONS

Johnson et al. "Using Fluorescent Compounds as Early Warning Detectors for Corrosion" Materials Performance, 1994, pp. 25-29, vol. 33, No. 4.

Barisci et al. "Conducting Polymers as a Basis for Responsive Materials Systems" Journal of Intelligent Material Systems and Structures, Sep. 1998, pp. 723-731, vol. 9, No. 9, Technomic Publ., Lancaster, PA, US.

"XP-002450740" Database WPI Week 1978-78927A, Sep. 26, 1978, Derwent Publications Ltd., London.

"XP-002450741" Database WPI Week 2003-620696, Dec. 13, 2002, Derwent Publications Ltd., London.

Agarwala, V. S., "Corrosion 'Health' Monitoring Systems for Reduced Maintenance/Repair and Increased System Reliability," Proc. Int. Conf. on Corrosion CONCORN(1997)pp. 140-150.

Davis, G. D.,et al., "Corrosion Protection and Condition Monitoring Using 'Smart' Appliques," Coatings & Linings, Materials Performance, 2004, pp. 32-36.

Zhang, Y., "Intelligent Coating for Nondestructive Structural Condition Monitoring," Sensors/Smart Materials, (2004) pp. 365-373.

Otto, J., et al., "Detection of Hidden Corrosion Under Paint," Nondestructive Characterization of Materials XI, Proceedings of the Int'l Symp. 11th, Berlin, Germany (2002 pp. 297-307.

Zanthos, M., et al., "Stimulation and Reaction. Functional Additives as Sensors in Smart Coatings," Farbe + Lack, (2003) pp. 21-23.

* cited by examiner

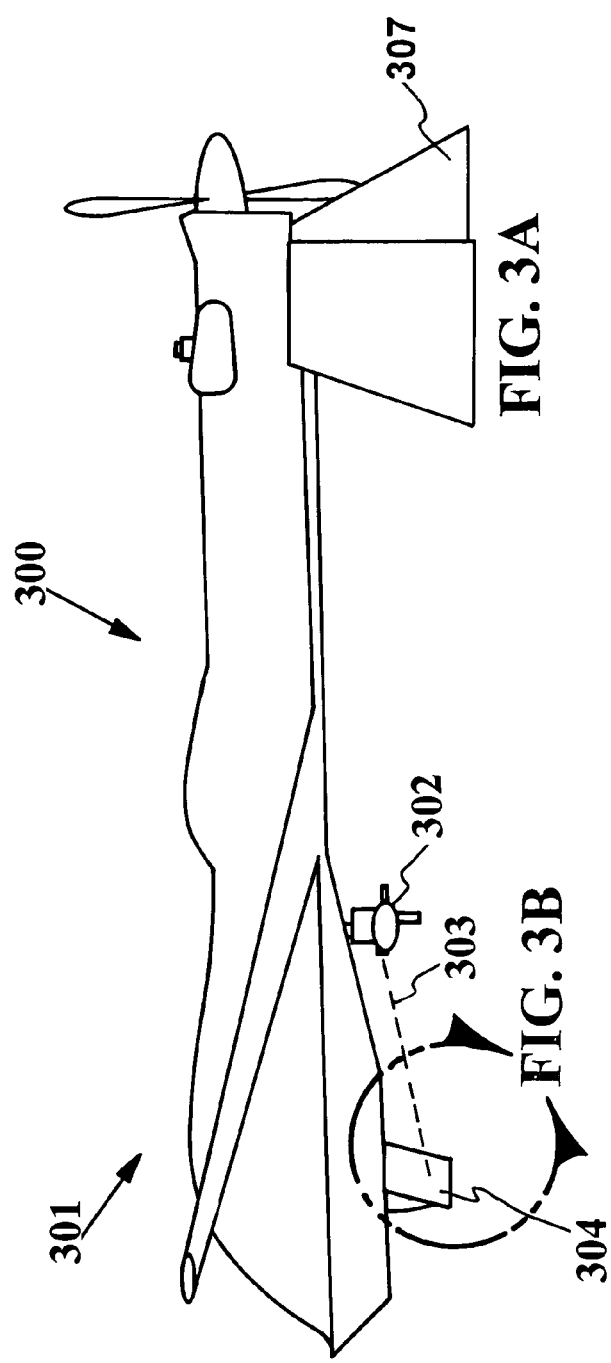
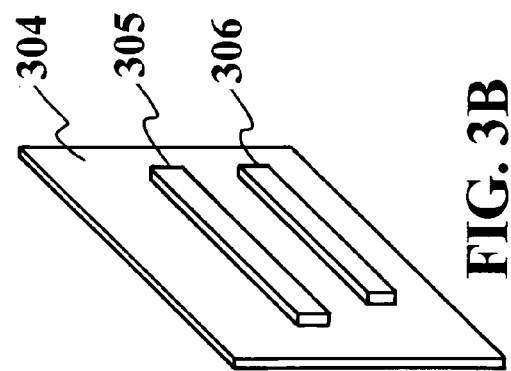
FIG. 3A
FIG. 3B

PAINT FOR DETECTION OF CORROSION AND WARNING OF CHEMICAL AND RADIOLOGICAL ATTACK

CROSS-REFERENCE TO RELATED APPLICATIONS

This application claims the benefit of U.S. Provisional Patent Application No. 60/711,488 filed Aug. 26, 2005 by Joseph C. Farmer and titled "Smart Surface & Intellicoat—Coatings for Detection of Hidden Corrosion/Cracking Damage & Warning of Chemical and Radiological Attack." U.S. Provisional Patent Application No. 60/711,488 filed Aug. 26, 2005 by Joseph C. Farmer and titled "Smart Surface & Intellicoat—Coatings for Detection of Hidden Corrosion/Cracking Damage & Warning of Chemical and Radiological Attack" is incorporated herein by this reference.

Related inventions are disclosed and claimed in the following co-pending application: U.S. patent application Ser. No. 11/293,657, filed Dec. 1, 2005, by Joseph C. Farmer, James Brunk, and S. Daniel Day, titled "Paint for Detection of Chemical or Radiological Agents," which is incorporated herein by reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to detection and more particularly to paint for detection of corrosion and chemical and radiological materials.

2. State of Technology

Corrosion damage is frequently hidden underneath protective paint coatings. It is reported that corrosion impacts 35,000 ground and tactical vehicles, 15,000 aircraft and helicopters, 1,000 strategic missiles, and 300 naval ships that have approximately 345 million square feet. Such deterioration is credited with mechanical failure of tactical vehicles, near sinking of naval ships, the crashes of several fighter jets in the 1980s, and the collapse of landing gear on several Navy jets during carrier operations. Corrosion-related maintenance activities involve approximately 700,000 military and civilian Department of Defense personnel, and several thousand commercial firms worldwide. Corrosion damage costs the Department of Defense $10-20 billion every year. In 1998, corrosion repair of helicopters cost approximately $4 billion alone. The earlier problems are found, the less expensive the repair.

Paints/coatings of the present invention enable the detection of chemical and radiological warfare agents through direct or instrument-assisted visual inspection. Such paints and coatings can warn soldiers of chemical and radiological attack. This feature can be added to tactical vehicles during maintenance operations. The use of paints inside buildings, trains, and subway tunnels would provide a means of detecting the presence of chemical and radiological warfare agents over large surfaces. Nerve agents are potent cholinesterase-inhibiting organophosphorous compounds. Symptoms of muscarinic and nicotinic overstimulation include abdominal pain, vomiting, diarrhea, excessive salivation and sweating, bronchospasm, copious pulmonary secretions, muscle fasciculations and weakness, and respiratory arrest. Seizures, bradycardia, or tachy-cardia may be present. Severe dehydration can result from volume loss due to sweating, vomiting, and diarrhea. Sequelae can include polyneuropathy and neuropsychiatric changes.

U.S. Pat. No. 5,935,862 to Thaddeus J. Novak issued Aug. 10, 1999 for microspot test methods and a field test kit for on-site inspections of chemical agents provides the following state of technology information: "Over the years, various highly toxic chemical warfare agents (CWA's) have been developed and stockpiled by several nations. In view of the biological hazards associated with CWA's and degradation products thereof, chemical warfare conventions (CWC's) have been developed by certain countries. These CWC's monitor, identify and, if necessary, dispose of CWA's which are not in compliance with the convention. As a result of the convention, it is often necessary to conduct inspections of various sites in order to assure compliance. In view of the advantages of rapidly and accurately identifying the presence of CWA's and associated by-products, and further in view of the need to address the shortcomings associated with currently available detection methods, there is still a need for new and improved detection methods and kits."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for warning of corrosion, chemical, or radiological substances. The system comprises painting a surface with a paint or coating that includes an indicator material and monitoring the surface for indications of the corrosion, chemical, or radiological substances. One embodiment of the present invention provides a system that comprises paint on a surface that warns of corrosion, chemical, or radiological substances. The paint is operatively connected to the surface and an indicator material carried by the paint provides an indication of the corrosion, chemical, or radiological substances. Throughout this application the terms paint(s) and coating(s) are used interchangeably.

Uses of the present invention include coatings for the detection of underlying corrosion and environmental cracking, coatings for the detection of chemical and radiological warfare agents, and coatings for the detection of environmental pollutants and chemical releases. The paints or coatings provide warning of corrosion, chemical, or radiological substances through direct or instrument-assisted visual inspection. Such paints and coatings can warn soldiers of chemical and radiological attack. This feature can be added to tactical vehicles during maintenance operations. The use of such paints inside buildings, trains, and subway tunnels provides a system for detecting the presence of chemical and radiological warfare agents over large surfaces.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIGS. 3A and 3B illustrate yet another embodiment of a system of the present invention.

DETAILED DESCRIPTION OF THE INVENTION

Figure 1:
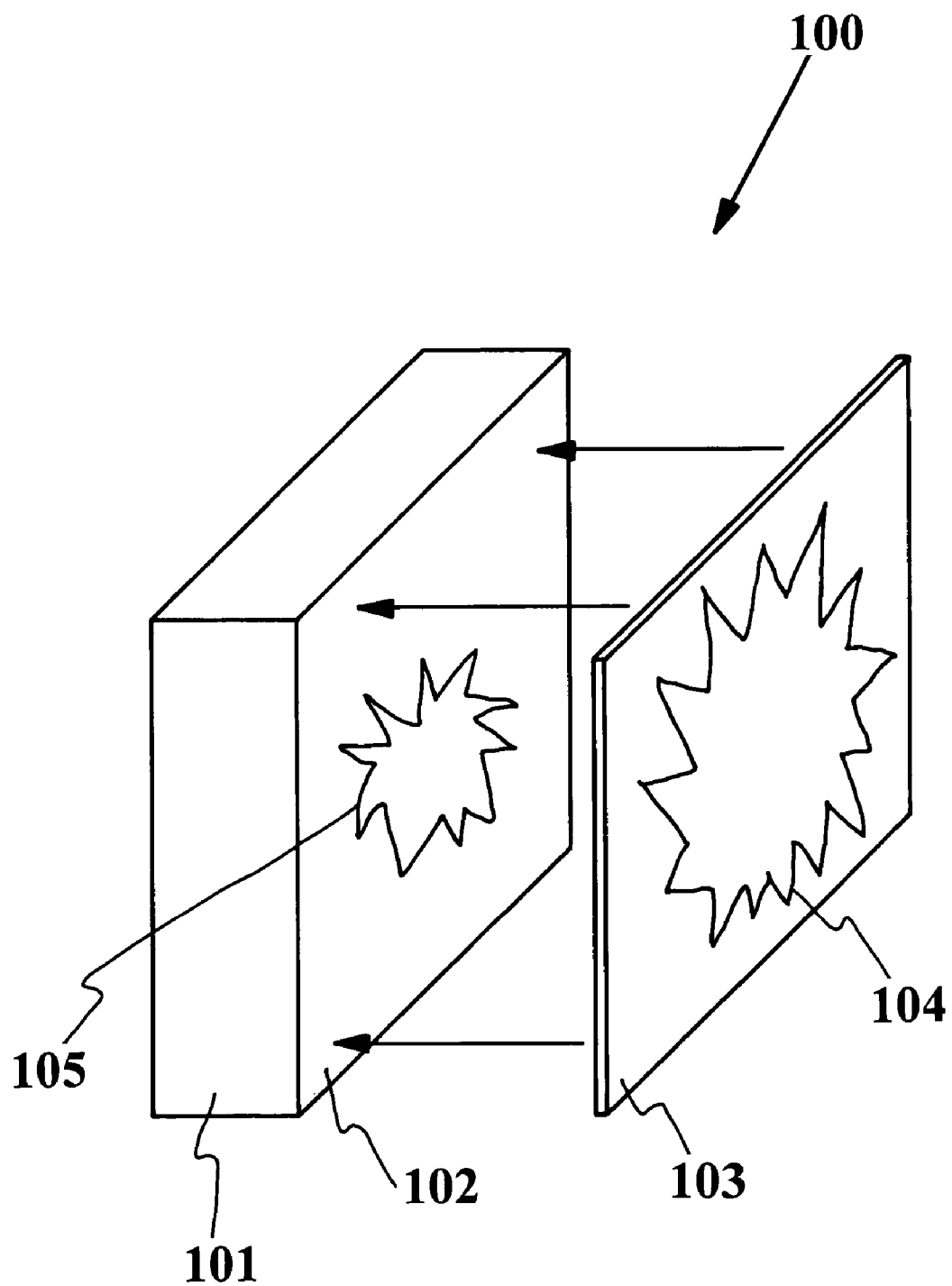
FIG. 1 illustrates an embodiment of a system of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring to the drawings and in particular to FIG. 1, an embodiment of a system of the present invention is illustrated. This embodiment of the system is designated generally by the reference numeral 100. The system 100 provides a warning of corrosion or environmental cracking on a structure 101. The corrosion or environmental cracking is illustrated by the irregular shaded area 105. The system 100 of warning of corrosion or environmental cracking comprises painting the relevant surface 102 with an indicator paint 103 and monitoring the paint 103 for indications of the corrosion or environmental cracking 105. The paint 103 contains material 104 that causes the paint to provide an indication of the corrosion or environmental cracking 105. For example the paint 103 could provide an indication of the corrosion or environmental cracking 105 by changing color.

Warning of corrosion or environmental cracking on a structure 101 is very useful and can provide a great benefit. Corrosion impacts 35,000 ground and tactical vehicles, 15,000 aircraft and helicopters, 1,000 strategic missiles, and 300 naval ships that have approximately 345 million square feet. Such deterioration is credited with mechanical failure of tactical vehicles, near sinking of naval ships, the crashes of several fighter jets in the 1980s, and the collapse of landing gear on several Navy jets during carrier operations. Corrosion-related maintenance activities involve approximately 700,000 military and civilian Department of Defense personnel, and several thousand commercial firms worldwide. Corrosion damage costs the Department of Defense $10-20 billion every year. In 1998, corrosion repair of helicopters cost approximately $4 billion alone. The earlier problems are found, the less expensive the repair.

The sensing coatings of the system 100 can reveal underlying damage during assisted visual inspection; corrosion can be detected with chemically sensitive fluorescent/colorimetric additives; and environmental cracking can be detected with train-sensitive coatings. Safe radiotracer could be used to track critical metal loss. Some of the paints and coatings of the present invention will enable the detection of corrosion and environmental cracking damage through direct or instrument-assisted visual inspection. Such coatings will provide pilots, sailors and soldiers with early warning of imminent failure through visual inspection. For example, this feature can be added to planes during routine terminal maintenance, and can be added to ships and submarines while in port, or during dry dock operations.

Corrosion damage, such as the corrosion or environmental cracking 105 illustrated in FIG. 1, is frequently hidden underneath protective paint coatings. Electronic corrosion sensors are unreliable, expensive, and difficult to install. Corrosion underneath coatings is accompanied by detectable chemical changes, such as lowered pH caused by the hydrolysis of dissolved polyvalent metal cations. The present invention provides chemically sensitive coatings 103 that can be applied during routine maintenance, and can be used as early indicators of corrosion.

In addition to detecting changes in pH, a wide variety of other functionality can be utilized for detecting corrosion damage. The paint 103 system fall into three broad classes: (1) chemically-sensitive additives to the coating, including pH sensitive indicators; (2) strain-sensitive coatings; and (3) radiological tracers capable of indicating critical losses/movement of metal. The material 104 in the paint 103 illustrated in FIG. 1 can be one or more of the following additives: Fluorescent Molecules & Particles (sensitive to pH & chloride); Semiconductor Clusters Inside Zeolite Cages (discrimination based upon molecular size); Electroactive Redox Couples (sensitive to electrochemical potential and oxidation state); Conductive Polymer Networks (sensitive to local potential and current due to corrosion); Materials with Anisotropic Dielectric (Optical and Electrical) Properties (sensitive to stress and strain); Various Radioisotope Tracers (sensitive to metal dissolution and movement); and Scintillation, Thermo-Luminescent, and Photo-Luminescent Pigments for Imaging the Movement of Radioisotope Tracers (sensitive to migration of dissolved metal).

One example of a safe radioisotope tracer metal-loss indicator is Tc-99, which emits beta particles during its decay. This material can be ion-implanted on the surfaces of critical structural components such as wing spars and lap joints on air planes. Crevice corrosion would cause the dissolution of the surface with the ion-implanted Tc-99, which in turn would cause the detectable movement of the ion-implanted radiotracer, thereby providing an unambiguous indication of metal loss. The extent of metal loss would be correlated with the strength of the scintillations associated with the beta decay. It would be possible to use other radioisotope tracers, including those emitting gamma rays. Specifically, the warning of corrosion or environmental cracking 105 on the structure 101 is accomplished by incorporating organic scintillation material 104 into the coating 103, capable of producing luminescence when irradiated with β-rays from the implanted Tc-99, dissolution and migration of the underlying metal can be imaged with the coating 103.

Applicants have tested embodiments of the present invention including the "intelligent coating" or "smart surface" concept illustrated in FIG. 1, which will enable the detection of small changes of pH at the coating-substrate interface that are indicative of crevice corrosion. Applicants made measurements of pH in crevice, showing that the pH may be very acidic, a change easily detected. Such measurements of pH were made with fiber optics probes, having fluorescent dye deposited on the tip. Ratiometric measurements of the fluorescence peaks are interpreted as pH. In the "intelligent coating" the pH sensitivity is directly incorporated into the coating 103. Other specific coatings will be developed to sense chemical warfare agents and will need "built-in" pH sensitivity to enable the detection of cholinesterase inhibitor.

Figure 2:
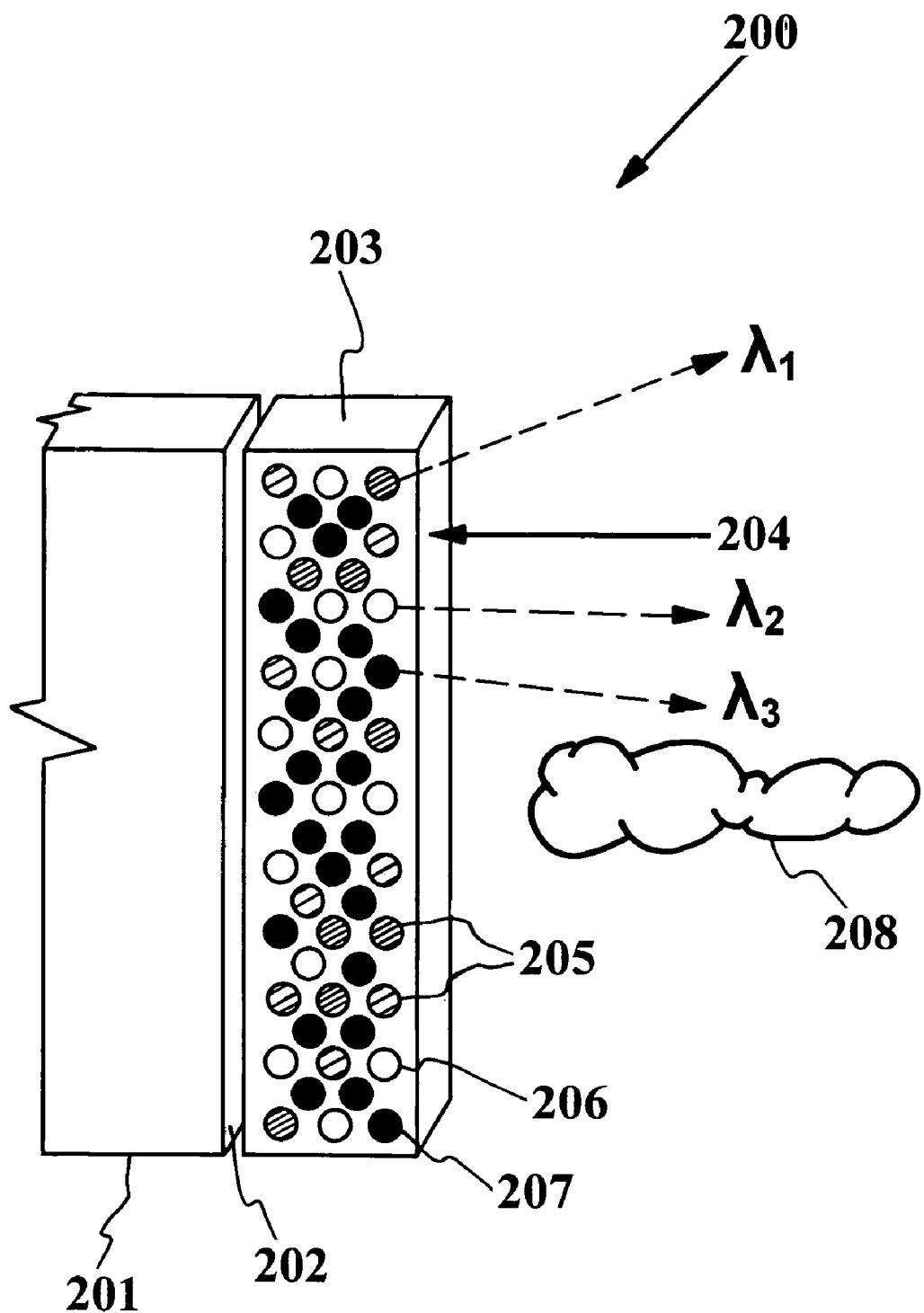
FIG. 2 illustrates another embodiment of a system of the present invention.

Referring to the drawings and in particular to FIG. 2, another embodiment of a system of the present invention is illustrated. This embodiment of the system is designated generally by the reference numeral 200. The system 200 provides a warning of chemical or radiological warfare agents. The system 200 of warning of chemical or radiological warfare agents comprises painting a surface 202 of a relevant structure 201 with an indicator paint 203 and monitoring the paint 203 for indications of the chemical or radiological warfare agents.

The paint 203 contains material that causes the paint to provide an indication of the chemical or radiological warfare agents. In Chemical Warfare Agents (CWA) detection, an alkyloxy methylphosphonic acid in the paint 203 is reacted with an appropriate dehydrating agent to produce cholinesterase inhibitor. The cholinesterase inhibitor is then detected with a pH-sensitive, chromogenic indicator molecule. The Chemical Warfare Agents (CWA) are illustrated by the cloud of CWA 208.

Referring again to FIG. 2, the detection of Chemical Warfare Agents (CWA) by the paint 203 will be described in greater detail. For example the CWA 208 can include nerve agents that are potent cholinesterase-inhibiting organophosphorous compounds. Symptoms of muscarinic and nicotinic overstimulation include abdominal pain, vomiting, diarrhea, excessive salivation and sweating, bronchospasm, copious pulmonary secretions, muscle fasciculations and weakness, and respiratory arrest. Seizures, bradycardia, or tachy-cardia may be present. Severe dehydration can result from volume loss due to sweating, vomiting, and diarrhea. Sequelae can include polyneuropathy and neuropsychiatric changes.

The system 200 imparts chemical sensitivity to the paint or coating 203 to enable the detection of the CWA 208. U.S. Pat. No. 5,935,862 to Thaddeus J. Novak and U.S. Pat. No. 6,403,329 to Thaddeus J. Novak et al describe an alkyloxy methylphosphonic acid that is reacted with appropriate dehydrating agents to produce cholinesterase inhibitor. U.S. Pat. No. 5,935,862 and U.S. Pat. No. 6,403,329 are incorporated herein by reference.

Some of the reagents involved used in the system 200 are: (1) Methylphosphonic Acid (MPA) & Alkyloxy Methylphosphonic Acids (AMPA), ethyl MPA (EMPA), isopropyl MPA (IMPA), cyclohexyl MPA (CMPA), pinacolyl MPA (PMPA), O-ethyl methylphosphonothioic acid (EMPTA), and 1,4-dithiane (DITHIANE); (2) Esterification Reagents, dialkyl sulfate, and dialkyl iodide; (3) Dehydrating & Other Reagents, 1,3-dicyclohexylcarbodiimide and 1,3-diisopropylcarbodiimide. (4) Chromogenic Detector Reagent, bromcresol green, 7,7,8,8-tetracyanoquinodimethane (TCNQ), and gold chloride with/without NaOH; and (5) Solid Absorbent, alumina and silica.

The cholinesterase inhibitor, produced by reacting AMPA with an appropriate dehydrating agent, is then detected with a pH-sensitive, chromogenic indicator molecule. Bromcresol green is a common chromogenic indicator, which is blue at $pH \geq 5.4$, and yellow at $3.8 < pH < 5.4$. The presence of cholinesterase inhibitor at the surface of the solid absorbent material lowers the pH from above 5.4 to an acidic level between 3.8 and 5.4, thereby producing a color change.

The system 200 for detection of chemical warfare agents utilizes the incorporation of the esterification and dehydration reagents into the coating 203 in a way to maintain their activity. This includes direct incorporation of the functionality into the polymeric coating, triggered release of the reagents from capsules, and transport-limited time-release.

The detection of Radiological Warfare Agents (RWA) utilizes the inclusion of scintillation agents into the paint 203. The Radiological Warfare Agents (RWA) are illustrated by the arrow 204. Special crystalline pigments 205, 206, and 207 are added to the paint 203 that produce luminescence $\lambda_1$, $\lambda_2$, and $\lambda_3$ when irradiated by alpha, beta and gamma rays 204. These scintillations can be detected directly with a photomultiplier tube (PMT) coupled with an amplifier and pulse-counting electronics, digital CCD-array cameras, or other such devices. Alternatively, the scintillation can be used to stimulate florescence in dyes that are incorporated within the polymeric binder of the paint. Alpha scintillation pigments 205 produce the luminescence $\lambda_1$ Beta scintillation pigments 206 produce the luminescence $\lambda_2$. Gamma scintillation pigments 207 produce the luminescence $\lambda_3$.

Referring again to FIG. 2, the detection of Radiological Warfare Agents (RWA) by the paint 203 will be described in greater detail. For example, radiological agents are detected through scintillation. The crystalline pigments 205, 206, and 207 are added to the paint 203 that produce luminescence $\lambda_1$, $\lambda_2$, and $\lambda_3$ when irradiated by alpha, beta and gamma rays 204. The luminescence can be detected directly with a PMT, digital CCD-array camera, or other such device, or used to stimulate florescence in dyes within the polymeric binder of the paint with detection of the secondary emission. Some of the components used in the system 200 are: (1) Inorganic Scintillators, such as LiI (Sn) for neutron detection, ZnS (Ag) for $\alpha$ detection, NaI (Ti) for $\gamma$ detection, CsI (Ti) for $\gamma$ detection, CsI (Na) for $\gamma$ detection, BGO for $\gamma$ detection, and $BaF_2$ for $\gamma$ detection; and (2) Organic Scintillators, such as anthracene for $\beta$ and neutron detection, trans-stillbene for $\beta$ detection, p-terphenyl for $\beta$ detection, diphenylorazole for $\beta$ and neutron detection, tetraphenyl butadiene for $\beta$ detection, and terphenyl in polystyrene for $\beta$ detection. These are incorporated into the paint 203, thereby imparting RWA sensitivity. It is to be understood that other active agents can also be exploited.

Applicant has successfully demonstrated radiation-sensitive paints of the present invention illustrated in FIG. 2. This has been accomplished with the successful detection of scintillations from painted surfaces irradiated by both alpha particles and gamma rays. Alpha particles from a weak 1-nCi plutonium-239 source were detected with a special scintillation paint formulation, a photomultiplier tube (PMT), and an appropriate pulse counting network. Parametric studies were performed, determining the scintillation rate as a function of coating thickness, and distance of separation between the coating and source. An optimum paint thickness was identified for this scenario. It was found that the paint has to be thick enough to provide an easily detectable level of scintillation, but not so thick that the scintillations undergo self-absorption by the paint before reaching the detector. Gamma rays from a 100-$\mu$Ci radium-226 source were also detected with another special scintillation paint formulation, by performing time-lapse photography with a commercially available 12.8-megapixel camera.

The paint illustrated by the system 100 and 200 illustrated in FIGS. 1 and 2 can be applied using various application techniques. For example, numerous methodologies can be used for the production of derivative-type paints and coatings for detecting the presence of radiological agents on or near surfaces, and for the production of "integrating" paints and coatings for quantifying long-term exposure to doses of radiation. These coatings incorporate scintillation and/or thermo-luminescent materials as pigments and can be easily produced with a variety of processes including organic polymeric binders, spray-on paints or coatings with organic polymeric binders, brush-on paints or coatings with organic polymeric binders, coatings and films produced with web coater and organic polymeric binders, powder coatings, inorganic ceramic/metallic binders, cold-spray processes, and thermal-spray processes.

The paints and coatings can be interrogated by any one of numerous systems. These include, but are not limited: (1) instantaneous detection of alpha-, beta- or gamma-induced scintillations from pigment particles with a PMT coupled to an amplifier and pulse-counting electronics, a digital CCD-array camera, or other such devices, for derivative-type coatings; or (2) laser-pulse, filament, or localized-microwave heating to induce photon emission from irradiated thermo-luminescent pigment particles, followed by detection with a PMT coupled to an amplifier and pulse-counting electronics, a digital CCD-array camera, or other such devices, for integral-type coatings, which integrate flux over the exposure time to provide a signal proportional to dose.

In regard to the detection of radioactive materials, the present invention illustrated by the system 100 and 200 illustrated in FIGS. 1 and 2 have may uses. For example radiation-sensitive paints and coatings can be used to monitor exposure in various scenarios of interest: (1) as paints for buildings and equipment in industrial plants involved in the production of nuclear and radiological materials; (2) as paints for the inside of nuclear power plants, nuclear powered ships, and submarines; (3) as paints for trucks and shipping containers and road-side facilities along shipping routes; (5) as paints for unmanned aerial vehicles, micro airships, and other surveillance devices; and (6) as paints for the detection and monitoring of activities involving radiological materials. In addition to enabling the long-term exposure (dose) of operating personnel in nuclear plants and nuclear-powered ships to be monitored, surfaces coated with these paints can be used to track and image the spread of radioactive contamination. Ultimately, thermo-luminescent paints and coatings could be used as a basis for qualifying the receipt of shipping containers for acceptance into the United States, where such qualification could be done through field interrogation of the painted surface, or through quantification of sampled paint chips.

These coatings can also be used on aircraft, to detect corrosion damage underneath protective coatings, by enabling the unexpected movement of ion-implanted tracers (such as Tc-99) to be detected and monitored.

Referring again to the drawings and in particular to FIGS. 3A and 3B, another embodiment of a system of the present invention is illustrated. This embodiment of the system is designated generally by the reference numeral 300. The system 300 provides a warning of chemical or radiological warfare agents encountered by an unmanned aerial vehicle (UAV) 301.

The UAV 301 is equipped with a camera 302. The camera 302 is moveable and can train its line of sight 303 to various locations including numerous locations on the body of the UAV 301. As illustrated in FIG. 3A, the camera line of sight 303 is trained on a viewing surface 304 on the body of the UAV 301. The camera line of sight 303 can be trained on other portions of the body of the UAV 301. For example an alternate viewing surface 307 is shown on one of the rear stabilizers of the UAV 301.

Referring now to FIG. 3B, the viewing surface 304 is shown in greater detail. The viewing surface 304 includes two paint strips 305 and 306.

The paint strip 305 is a paint strip for chemical detection and the paint strip 306 is a paint strip for radiation detection. The paint strip 305 for chemical detection contains material that causes the paint to provide an indication of the chemical warfare agents. Paint for chemical detection has been described previously in connection with FIG. 2 and that description is incorporated in this description of the paint strip 305 of the system 300. The paint strip 306 for radiation detection contains material that causes the paint to provide an indication of the radiation warfare agents. Paint for radiation detection has been described previously in connection with FIG. 2 and that description is incorporated in this description of the paint strip 306 of the system 300.

By monitoring the viewing area 304 with the camera 303, it is possible to monitor whether the UAV 301 has encountered chemical warfare agents or radiation warfare agents. Since UAVs are routinely equipped with cameras and the cameras and the cameras are moveable to view various portions of the body of the UAV, the addition of the system 300 provides a warning of chemical or radiological warfare agents is a simple and cost effective system. The system 300 can be retrofitted to existing UAVs with a minimum of cost and time.

Figure 4:
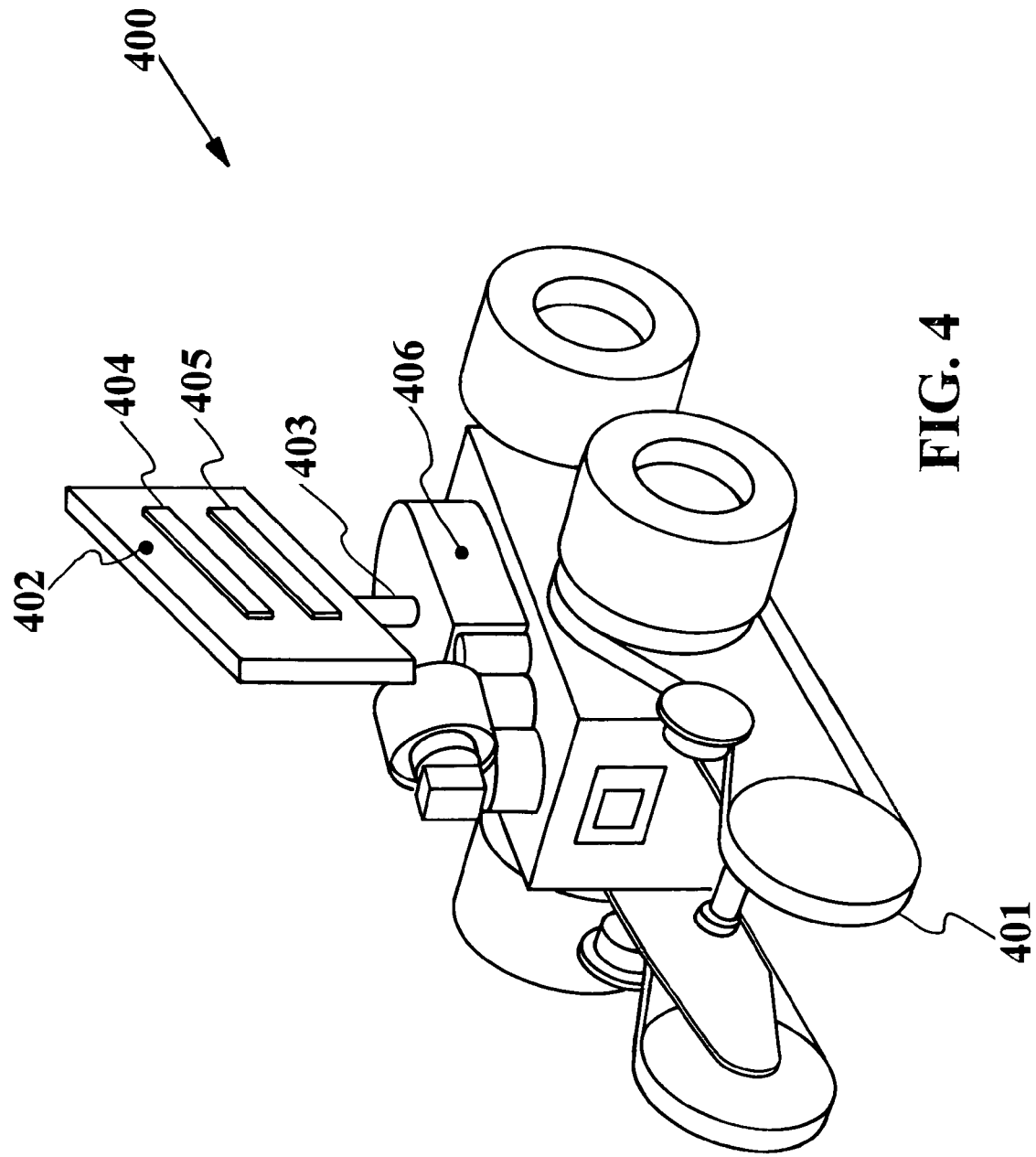
FIG. 4 illustrates another embodiment of a system of the present invention.

Referring again to the drawings and in particular to FIG. 4, another embodiment of a system of the present invention is illustrated. This embodiment of the system is designated generally by the reference numeral 400. The system 400 provides a warning of chemical or radiological warfare agents encountered by a robot vehicle 401.

The robot vehicle 401 includes a screen 402. The screen 402 is moveable on a pedestal 403. The screen 402 can be turned to provide a line of sight from a viewer's location. The screen 402 includes two paint strips 404 and 405.

The paint strip 404 is a paint strip for chemical detection and the paint strip 405 is a paint strip for radiation detection. The paint strip 404 for chemical detection contains material that causes the paint to provide an indication of the chemical warfare agents. Paint for chemical detection has been described previously in connection with FIG. 2 and that description is incorporated in this description of the paint strip 404 of the system 400. The paint strip 405 for radiation detection contains material that causes the paint to provide an indication of the radiation warfare agents. Paint for radiation detection has been described previously in connection with FIG. 2 and that description is incorporated in this description of the paint strip 405 of the system 400.

By monitoring the screen 402, it is possible to monitor whether the robot vehicle 401 has encountered chemical warfare agents or radiation warfare agents. Robot vehicle are routinely use for investigating suspicious packages or areas. The addition of the system 400 to a robot vehicle provides a warning of chemical or radiological warfare agents that is simple and cost effective. Instead of a viewing screen 402, the robot vehicle 401 can have an alternate viewing surface 407 on the existing body of the robot vehicle 401. The system 400 can be retrofitted to existing robot vehicles with a minimum of cost and time.

Referring again to FIGS. 1, 2, 3A, 3B, and 4, embodiments of systems of the present invention for warning of corrosion, chemical, or radiological substances have been described. The systems comprise painting a surface with an indicator material and monitoring said surface for indications of the corrosion, chemical, or radiological substances. In one embodiment the indicator material provides chemically-sensitive additives that provide pH sensitive indicators, or that provide a strain-sensitive coating, or that provide radiological tracers capable of indicating critical losses movement of metal. In another embodiment the indicator material provides chemical-sensitive additives or coatings: fluorescent molecules and particles, semiconductor clusters inside zeolite cages, electroactive redox couples, conductive polymer networks, incorporation in single protective corrosion-sensing coating, strain-sensitive coating, birefringence, conductivity, unambiguous beta-decay metal-loss tracer, or movement of ion-implanted Tc-99 under coating.

The embodiments of systems of the present invention illustrated in FIGS. 1, 2, 3A, 3B, and 4 include synthesis and production of radiation-sensitive pigments including at least one of the growth of bulk crystals followed by milling in inert cryogen liquids or nucleation and precipitation from the gas phase or nucleation and precipitation from the liquid phase. Other embodiments include dispersing pigments uniformly and homogeneously in paint solutions for application by brush or spray using surfactant or ultrasonics or agitation by gas sparging or impeller. Other embodiments include applying organic-type paints or coatings with scintillation, thermo-luminescent or photoluminescent pigments including brushing, spraying, dipping, electrophoretic deposition, or electrochemical deposition. Other embodiments include applying inorganic-type films or coatings with scintillation, thermo-luminescent or photo-luminescent materials including physical vapor deposition, including evaporation or magnetron sputtering or chemical vapor deposition or electrochemical deposition or cold spray particles suspended in high-velocity gas streams or thermal spray including flame spray, plasma spray, wire-arc, high-velocity oxy-fuel, or detonation gun processes. Other embodiments include applying inorganic-type films or coatings with sensitivity to corrosion and environmental cracking, based upon sensitivity to pH, chloride, dissolved metal cations, electrochemical potential, oxidation state, stress and strain including physical vapor deposition or evaporation or magnetron sputtering or chemical vapor deposition or electrochemical deposition or cold spray particles suspended in high-velocity gas streams or thermal spray including flame spray, plasma spray, wire-arc, high-velocity oxy-fuel, or detonation gun processes. Other embodiments include applying materials sensitive to chemical warfare agents as inorganic coatings with processes including physical vapor deposition including evaporation and magnetron sputtering, chemical vapor deposition, electrochemical deposition, cold spray particles suspended in high-velocity gas streams, or thermal spray including flame spray, plasma spray, wire-arc, high-velocity oxy-fuel, or detonation gun processes wherein said materials will be infiltrated with reagents that react with the chemical warfare agents to produce changes in pH that can be detected with calorimetric and ratiometric fluorescent indicators.

The embodiments of systems of the present invention illustrated in FIGS. 1, 2, 3A, 3B, and 4 include the step of a paint-chip sample taken and the organic matrix and shield coating dissolved wherein upon heating each pigment particle will release a pulse of photons at its characteristic wavelength with the detected photon pulses at each characteristic wavelength representing a particular band of radiation energy. Other embodiments include the step of interrogating of derivative-type coatings with scintillation pigments, including embedded fiber optics, embedded photodiodes, stand-off optics with PMT with amplifier and pulse counting, or digital CCD-array camera with time-lapse exposure. Other embodiments include the step of interrogating integral-type coatings with thermo-luminescent pigments, including laser-pulse, localized-filament, or localized microwave heating, followed by detection with embedded fiber optics, embedded photodiodes, stand-off optics with PMT with amplifier and pulse counting, or digital CCD-array camera with time-lapse exposure.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system that warns of encounter of radiological substances, comprising:
   an unmanned aerial vehicle,
   a discrete viewing surface on said unmanned aerial vehicle,
   a paint operatively connected to said discrete viewing surface on said unmanned aerial vehicle,
   an indicator material carried by said paint that provides a direct or instrument-assisted visual indication of radiological substances encountered by said unmanned aerial vehicle,
   wherein, said indicator material carried by said paint includes scintillation pigments that produces luminescence when exposed to radiological substances and produces a direct or instrument-assisted visual indication of the radiological substances on said paint on said discrete viewing surface on said vehicle, and a camera operatively connected to said unmanned aerial vehicle for monitoring said paint on said discrete viewing surface on said unmanned aerial vehicle.

2. A system that warns of encounter of radiological substances, comprising:
   a robot vehicle,
   a discrete viewing surface on said robot vehicle,
   a paint operatively connected to said discrete viewing surface on said robot vehicle,
   an indicator material carried by said paint that provides an indication of the radiological substances encountered by said robot vehicle,
   wherein said indicator material carried by said paint includes scintillation pigments that produces luminescence when exposed to radiological substances and produces a direct or instrument-assisted visual indication of the radiological substances on said paint on said discrete viewing surface on said vehicle, and
   a camera operatively connected to said robot vehicle for monitoring said paint on said discrete viewing surface on said robot vehicle.

3. A system that warns of radiological substances, comprising:
   a vehicle, wherein said vehicle is a nuclear powered ship, a submarine, a truck, an unmanned aerial vehicle, a micro airship, a surveillance vehicle, or a robot vehicle,
   a discrete viewing surface on said vehicle,
   a paint operatively connected to said discrete viewing surface on said vehicle, and an indicator material carried by said paint that provides an indication of the radiological substances, wherein said indicator material includes scintillation pigments that produces luminescence when exposed to radiological substances and produces a direct or instrument-assisted visual indication of the radiological substances on said paint on said discrete viewing surface on said vehicle.

4. The system that warns of radiological substances of claim 3 wherein said scintillation pigments includes crystalline pigments that produce luminescence when irradiated by beta rays.

5. The system that warns of radiological substances of claim 3 wherein said scintillation pigments includes crystalline pigments that produce luminescence when irradiated by gamma rays.

6. The system that warns of radiological substances of claim 3 including a camera operatively connected to said vehicle for monitoring said paint.

* * * * *